(12) United States Patent
Nishigishi

(10) Patent No.: US 10,363,391 B2
(45) Date of Patent: Jul. 30, 2019

(54) CATHETER

(71) Applicant: ASAHI INTECC CO., LTD., Seto-shi, Aichi (JP)

(72) Inventor: Makoto Nishigishi, Owariasahi (JP)

(73) Assignee: ASAHI INTECC CO., LTD., Seto-shi (JP)

(*) Notice: Subject to any disclaimer, the term of this patent is extended or adjusted under 35 U.S.C. 154(b) by 0 days.

(21) Appl. No.: 15/887,139

(22) Filed: Feb. 2, 2018

(65) Prior Publication Data
US 2018/0154107 A1     Jun. 7, 2018

Related U.S. Application Data

(63) Continuation of application No. 14/725,402, filed on May 29, 2015, now Pat. No. 9,919,128.

(30) Foreign Application Priority Data

Jul. 29, 2014 (JP) .................. 2014-153952

(51) Int. Cl.
  *A61M 25/00* (2006.01)
  *A61M 25/10* (2013.01)
  *A61M 25/01* (2006.01)

(52) U.S. Cl.
  CPC ...... *A61M 25/005* (2013.01); *A61M 25/0053* (2013.01); *A61M 25/0054* (2013.01);
  (Continued)

(58) Field of Classification Search
  CPC ............ A61M 25/005; A61M 25/0147; A61M 25/0102; A61M 25/0054; A61M 25/10;
  (Continued)

(56) References Cited

U.S. PATENT DOCUMENTS 6,299,595 B1    10/2001  Dutta et al.
6,702,781 B1 *   3/2004  Reifart ................ A61M 25/104
                                                      604/96.01
(Continued)

FOREIGN PATENT DOCUMENTS

EP    1 676 594 A1    7/2006
EP    2 341 974 B1    9/2014
(Continued)

OTHER PUBLICATIONS

Dec. 8, 2015 Extended European Search Report issued in European Patent Application No. 15170289.1.
(Continued)

*Primary Examiner* — Amber R Stiles
(74) *Attorney, Agent, or Firm* — Oliff PLC

(57) ABSTRACT

A catheter including an outer tube; a first inner tube disposed within the outer tube; a second inner tube disposed within the outer tube and parallel to the first inner tube, and having an insertion opening at its proximal end and a distal end opening at its distal end; and a first core wire and a second core wire disposed between the first inner tube and an outer tube. The second inner tube extends from a medial region of the catheter to a distal end of the catheter. A distal end of the first core wire is located distal to the insertion opening of the second inner tube, and a distal end of the second core wire is located proximal to the insertion opening of the second inner tube. The second core wire can move between the outer tube and the first inner tube.

16 Claims, 10 Drawing Sheets

(52) U.S. Cl.
CPC .... *A61M 25/0102* (2013.01); *A61M 25/0147* (2013.01); *A61M 25/10* (2013.01); *A61M 2025/0004* (2013.01); *A61M 2025/0059* (2013.01); *A61M 2025/0063* (2013.01); *A61M 2210/1042* (2013.01); *A61M 2210/12* (2013.01)

(58) Field of Classification Search
CPC ...... A61M 25/0053; A61M 2025/0063; A61M 2210/12; A61M 2025/0059; A61M 2210/1042
See application file for complete search history.

(56) References Cited

U.S. PATENT DOCUMENTS

| | | |
|---|---|---|
| 9,084,869 B2 | 7/2015 | Anderson et al. |
| 2002/0165571 A1 | 11/2002 | Hebert et al. |
| 2004/0116848 A1 | 6/2004 | Gardeski et al. |
| 2005/0267408 A1 | 12/2005 | Grandt et al. |
| 2007/0073331 A1* | 3/2007 | Brown .................. A61F 2/958 606/194 |
| 2008/0188800 A1 | 8/2008 | Bencini et al. |
| 2011/0196298 A1 | 8/2011 | Anderson et al. |
| 2013/0211385 A1 | 8/2013 | Lazarus |

FOREIGN PATENT DOCUMENTS

| | | |
|---|---|---|
| JP | H09-510894 A | 11/1997 |
| JP | 2012-506738 A | 3/2012 |
| JP | 2012-213627 A | 11/2012 |
| JP | 2012-223207 A | 11/2012 |
| WO | 95/26213 A1 | 10/1995 |
| WO | 2006/126642 A1 | 11/2006 |
| WO | 2010/048676 A1 | 5/2010 |
| WO | 2012/068505 A1 | 5/2012 |

OTHER PUBLICATIONS

Jan. 13, 2017 Office Action issued in Japanese Patent Application No. 2014-153952.
Feb. 3, 2017 Extended European Search Report issued in European Patent Application No. 16193271.0.
Jun. 27, 2017 Office Action issued in U.S. Appl. No. 14/725,402.
Aug. 1, 2017 Office Action issued in Japanese Patent Application No. 2014-153952.
Mar. 28, 2018 Office Action issued in Chinese Application No. 201510301054.6.
Jun. 26, 2018 Office Action issued in Japanese Patent Application No. 2017-192127.
Nov. 26, 2018 Office Action issued in Chinese Patent Application No. 201510301054.6.

* cited by examiner

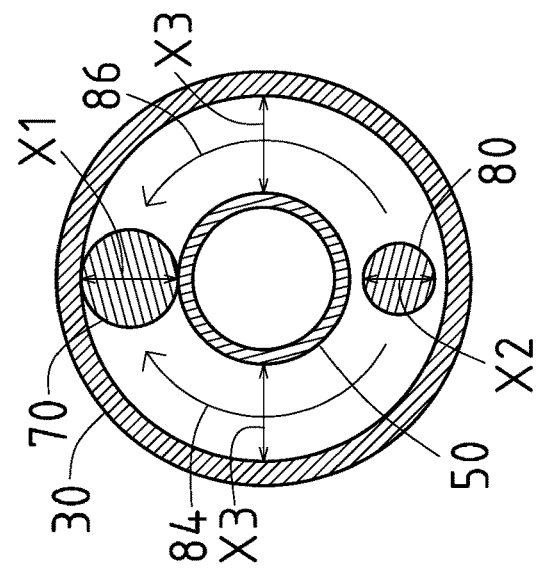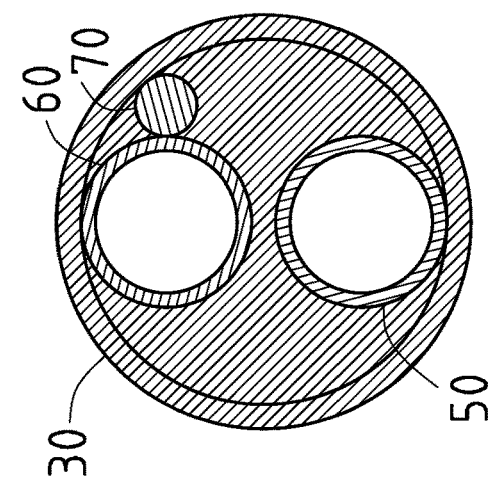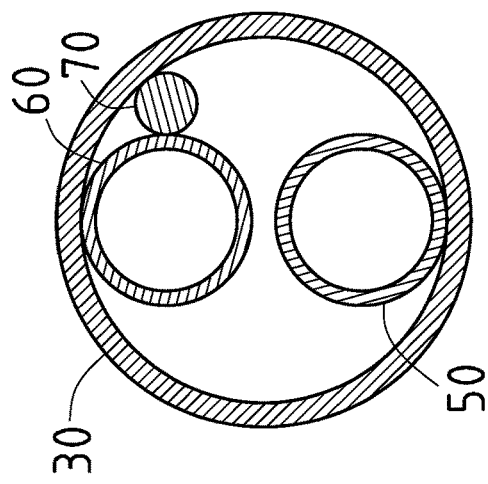

CATHETER

CROSS REFERENCE TO RELATED APPLICATIONS

This is a Continuation of application Ser. No. 14/725,402 filed on May 29, 2015, which claims priority to Japanese Application No. 2014-153952 filed on Jul. 29, 2014. The disclosure of the prior applications is hereby incorporated by reference herein in its entirety.

BACKGROUND

The disclosed embodiments relate to a medical device. Specifically, the disclosed embodiments relate to a catheter capable of efficiently transmitting an operator's pushing force to a distal end of the catheter, and capable of bending along curved regions of a blood vessel, bile duct, pancreatic duct or the like.

When a narrowed or obstructed segment is formed in a lumen (e.g., a blood vessel, bile duct, pancreatic duct, or the like), the flow of fluid (e.g., blood, bile (gall), pancreatic fluid, or the like) through the lumen may be hindered. Traditionally, treatments with a catheter have been widely performed to treat a narrowed or obstructed segment of a lumen. In order for the catheter to reach the narrowed or obstructed segment, the operator's pushing force needs to be efficiently transmitted to the distal end of the catheter. It is also important to avoid catching the catheter in a curved region of the lumen as the catheter is being pushed.

In order to improve the pushing force toward the distal end of the catheter, the catheter may include a core wire axially disposed between an outer tube and an inner tube. See, for example, WO 2006/126642 and Japanese Patent Application Laid-Open No. 2012-223207. One core wire is disposed in the catheter of WO 2006/126642, and multiple core wires are disposed in the catheter of Japanese Patent Application Laid-Open No. 2012-223207.

However, in the catheters of WO 2006/126642 and Japanese Patent Application Laid-Open No. 2012-223207, the core wire or wires are fixed to other members of the catheter (for example, the outer tube, the inner tube, a hypo tube, or the like), and thus have almost no degree of freedom. Therefore, when the catheter is inserted into a curved region of a lumen, the core wires cannot move to the optimal position within the catheter, causing the core wire to break. Additionally, the catheter may get caught in the curved region of the lumen when being pushed, preventing the catheter from reaching the target narrowed or obstructed segment.

Furthermore, although axial rigidity can be improved by using multiple core wires, the multiple core wires may interfere with each other (i.e., obstruct each other's movement) when the catheter is inserted into a curved region of a lumen. Significantly, this may prevent the catheter from bending along the lumen, preventing the catheter from reaching the target narrowed or obstructed segment.

SUMMARY

The disclosed embodiments have been devised in view of the above circumstances. An object of the disclosed embodiments is to provide a catheter having multiple core wires with a reduced risk that the core wires will interfere with each other. In the catheter, a second core wire is capable of moving between an outer tube and an inner tube of the catheter. As a result, the operator's pushing force can be efficiently transmitted to the distal end of the catheter, and there is a reduced risk of that the catheter will get caught in a curved region of a lumen when being pushed.

The disclosed embodiments address the above problems. In particular, a catheter of the disclosed embodiments comprises an outer tube, an inner tube inserted into the outer tube, a first core wire inserted between the outer tube and the inner tube, and a second core wire inserted parallel to the first core wire. The first core wire is fixed to the outer tube or the inner tube, while the second core wire is capable of moving in the axial direction of the catheter and circumferentially around the inner tube. By providing the fixed first core wire and the movable second core wire, axial rigidity can be improved so that the operator's pushing force is efficiently transmitted to the distal end of the catheter. Additionally, the second core wire can move to the optimal position when the catheter is inserted into a curved region of a lumen. There is therefore a reduced risk that the first core wire and the second core wire will interfere with each other, which would prevent the catheter from bending along the lumen and potentially cause one or both of the first core wire and the second core wire to break.

The catheter may include a portion in which a cross-sectional area of the second core wire is smaller than a cross-sectional area of the first core wire. The second core wire can thus easily move to the optimal position even when the shape of the catheter is deformed due to an external force exerted on the catheter when the catheter is inserted into a curved region of a lumen. This further reduces the risk that the catheter will get caught in a curved region of the lumen.

The catheter may also include a restriction part provided at the first core wire or the second core wire. The restriction part restricts the movement of the second core wire toward the distal end of the catheter. This reduces the risk that the second core wire will project out of the outer tube when an operator pushes the catheter in the distal direction. Moreover, a force that drives the second core wire in the distal direction can be transmitted to the outer tube or the inner tube through the restriction part, improving the pushing force transmitted to the distal end of the catheter.

The restriction part may be provided at the second core wire, and positioned proximally to a proximal end of the first core wire or a proximal end of the outer tube. This further reduces the risk that the second core wire will project out of the outer tube because the restriction part cannot move past the proximal end of the first core wire or the proximal end of the outer tube when the operator pushes the catheter in the distal direction.

BRIEF DESCRIPTION OF THE DRAWINGS

FIGS. 2A to 2C are cross-sectional views taken along lines A-A, B-B, and C-C, respectively, of FIG. 1.

DETAILED DESCRIPTION OF EMBODIMENTS

Figure 1:
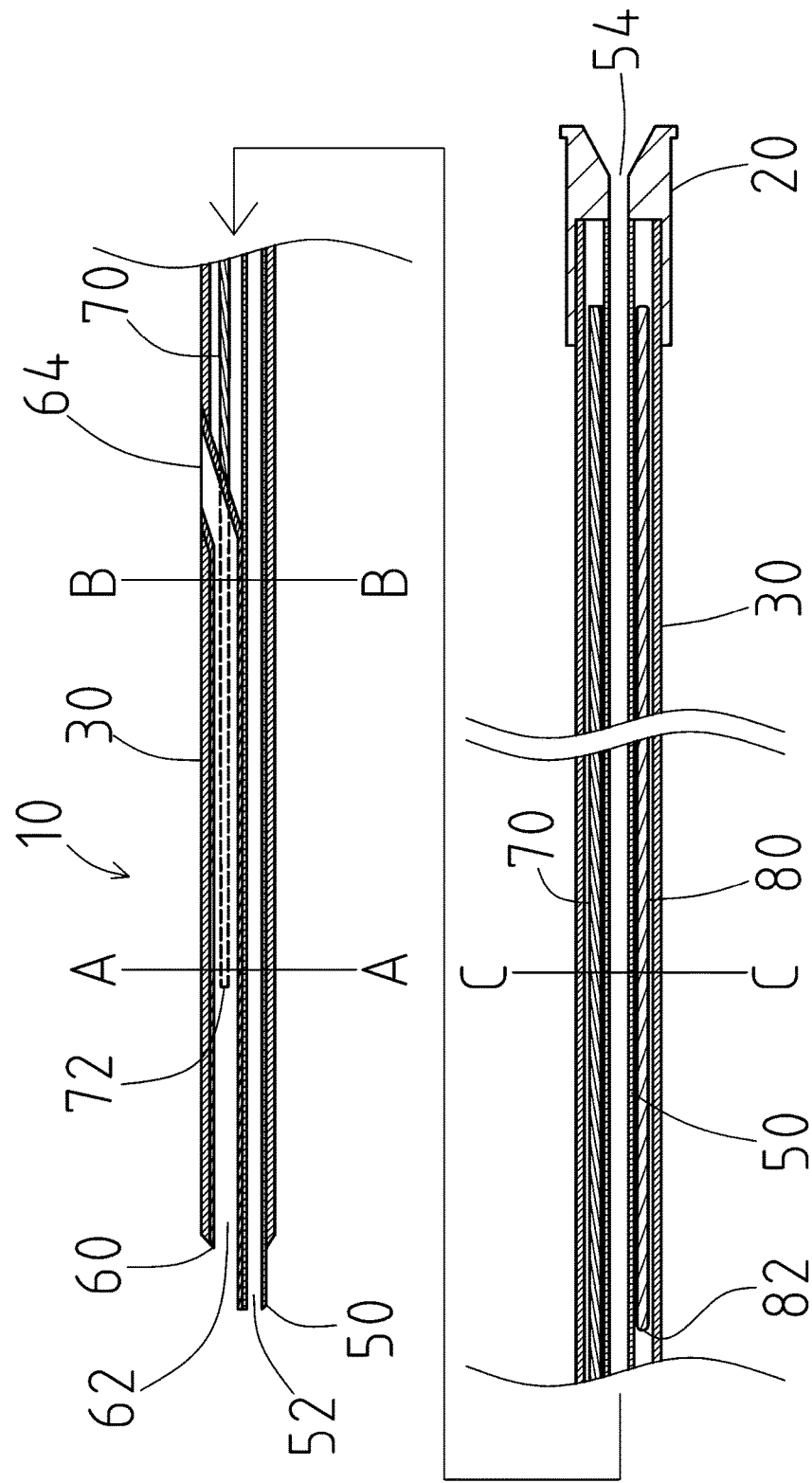
FIG. 1 shows an overall view of a catheter according to the disclosed embodiments.

A catheter 10 of the disclosed embodiments is described with reference to FIGS. 1 to 3. The left side in FIG. 1 corresponds to the distal end (the front end), which is to be inserted into the body, and the right side corresponds to the proximal end (the base end), which is to be operated by an operator such as a physician.

The catheter 10 may be used for treating, for example, a narrowed or obstructed segment formed in a lumen (e.g., a blood vessel, bile duct, pancreatic duct or the like). As shown in FIG. 1, the catheter 10 mainly comprises a connector 20, an outer tube 30, a first inner tube 50, a second inner tube 60, a first core wire 70, and a second core wire 80.

The first inner tube 50 is inserted into the outer tube 30 throughout almost the full length of the catheter 10. A guide wire may be inserted into the first inner tube 50. In order to allow for easy insertion of the guide wire, the connector 20 is connected to the proximal end of the outer tube 30 and the proximal end of the first inner tube 50. A first distal end opening 52 is provided at the distal end of the first inner tube 50, and a first insertion opening 54 is provided at the proximal end of the first inner tube 50 through the connector 20.

The second inner tube 60 is inserted into the outer tube 30 parallel to the first inner tube 50 from a medial region of the catheter 10 through the distal end of the catheter 10. As in the first inner tube 50, a guide wire may also be inserted into the second inner tube 60. A second distal end opening 62 is provided at a distal end of the second inner tube 60, and a second insertion opening 64 is provided at a proximal end of the second inner tube 60.

The outer tube 30, the first inner tube 50, and the second inner tube 60 may be formed with a thermoplastic resin. For example, a resin such as a polyamide, polyamide elastomer, polyolefin, polyester, polyester elastomer, or nylon can be used.

The first inner tube 50 extends throughout almost the full length of the catheter 10. It may therefore be difficult for an operator to replace a guide wire inserted into the first inner tube 50. On the other hand, the rigidity of the catheter 10 is advantageously improved when a guide wire is inserted into the first inner tube 50, allowing the operator to easily push the catheter 10 in the distal direction.

Moreover, the second inner tube 60 extends only from a medial region of the catheter 10 to the distal end of the catheter 10, and not along the full length of the catheter 10. The operator can therefore easily replace a guide wire inserted into the second inner tube 60. However, the insertion of a guide wire into the second inner tube 60 improves the rigidity of the catheter 10 only at the distal portion of the catheter 10. Therefore, if a guide wire is inserted only into the second inner tube 60, the catheter 10 may break near the second insertion opening 64 of the second inner tube 60 where the rigidity suddenly changes when an operator pushes the catheter 10 in the distal direction.

However, because the catheter 10 comprises both the first inner tube 50 and the second inner tube 60, an operator can readily replace a second guide wire inserted into the second inner tube 60 while maintaining a state where a first guide wire is inserted into the first inner tube 50. Thus, the operator can both readily replace the second guide wire and at the same time easily push the catheter 10 in the distal direction.

As shown in FIG. 1, the first core wire 70 and the second core wire 80 are inserted into the catheter 10 between the outer tube 30 and the first inner tube 50 and extend in the axial direction. The first core wire 70 and the second core wire 80 may each have a circular cross section. For example, the first core wire 70 and the second core wire 80 may each be a tapered metal wire member in which the diameter becomes smaller toward the distal end. There is no particular limitation for the material of the first core wire 70 and the second core wire 80. For example, stainless steel or a superelastic alloy such as an Ni—Ti alloy can be used.

The first core wire 70 is longer than the second core wire 80. Therefore, a distal end 72 of the first core wire 70 is located distally to the second insertion opening 64 of the second inner tube 60, while a distal end 82 of the second core wire 80 is located proximally to the second insertion opening 64 of the second inner tube 60.

FIGS. 2A to 2C are cross-sectional views taken along lines A-A, B-B, and C-C, respectively, of FIG. 1. The first core wire 70 is fixed to the outer tube 30 near the second insertion opening 64 of the second inner tube 60 (see FIG. 2B). Therefore, the first core wire 70 does not move in the axial or circumferential direction when an operator operates the catheter 10.

The second core wire 80 inserted parallel to the first core wire 70 is not fixed to either the outer tube 30 or the first inner tube 50 (see FIG. 1 and FIG. 2C). Therefore, the second core wire 80 can move in the axial and circumferential directions between the outer tube 30 and the first inner tube 50 when an operator operates the catheter 10. As shown in FIG. 2C, the second core wire 80 can move in either of the clockwise direction as shown by an arrow 84 or the counterclockwise direction as shown by an arrow 86.

Figure 3A:
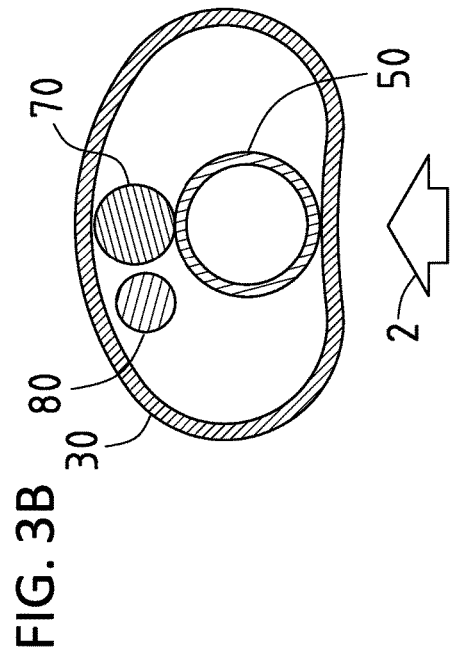
FIGS. 3A to 3D show how the second core wire moves in a circumferential direction when an external force is exerted onto the catheter.
Figure 3B:
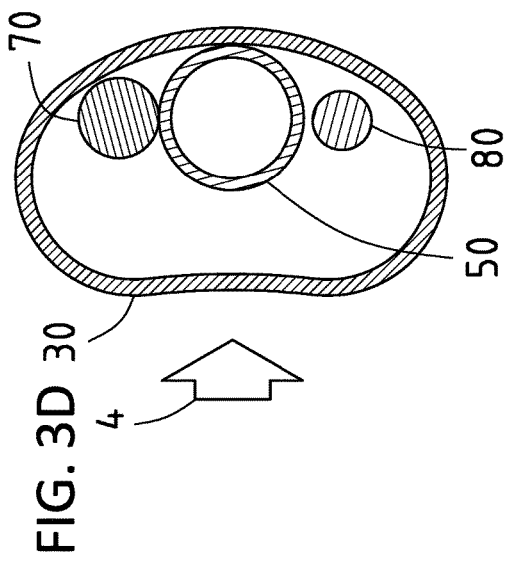
Figure 3C:
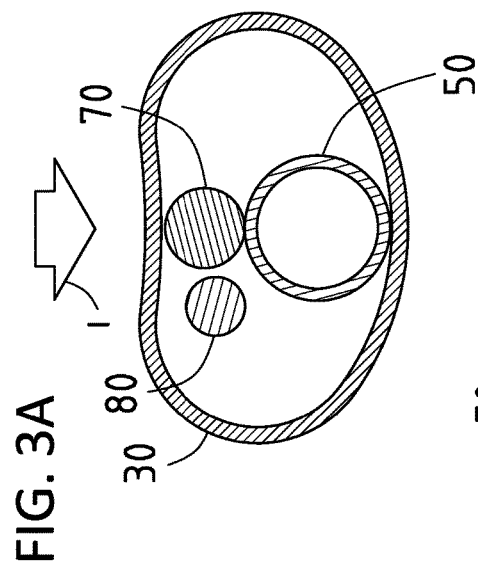
Figure 3D:
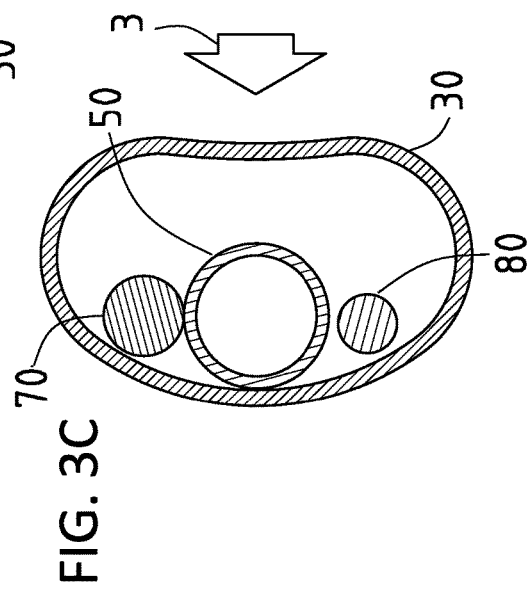

FIGS. 3A to 3D show how the second core wire 80 moves in a circumferential direction when external forces 1, 2, 3 and 4 are exerted on the catheter by a curved region of a lumen. FIGS. 3A to 3D are cross-sectional views taken along line C-C of FIG. 1, as in FIG. 2C. As shown in FIGS. 3A and 3B, when the external forces 1 and 2 are exerted on the catheter 10 by a curved region of a lumen, the outer tube 30 changes into a horizontally elongated ellipsoidal shape due to the external forces 1 and 2. Therefore, the second core wire 80 tends to move to, for example, a position where the first core wire 70 and the second core wire 80 are horizontally aligned. Meanwhile, as shown in FIGS. 3C and 3D, when the external forces 3 and 4 are exerted on the catheter 10 by a curved region of a lumen, the outer tube 30 changes into a vertically elongated ellipsoidal shape due to the external forces 3 and 4. Therefore, the second core wire 80 tends to move to, for example, a position where the first core wire 70, the second core wire 80, and the first inner tube 50 are vertically aligned (in other words, the second core wire 80 is disposed symmetrically with respect to the first core wire 70 relative to the first inner tube 50).

As described above, the catheter 10 has a configuration in which the second core wire 80 can move to the optimal position depending on the external forces 1, 2, 3, and 4 exerted at a curved region of the lumen when the catheter 10 is inserted into the lumen. This reduces the risk that the first core wire 70 and the second core wire 80 will interfere with each other, which would prevent the catheter 10 from bending along a curved region of a lumen and potentially cause one or both of the first core wire 70 and the second core wire 80 to break. Moreover, both the first core wire 70

(fixed to the outer tube 30) and the second core wire 80 (not fixed to the outer tube 30) are disposed between the outer tube 30 and the first inner tube 50 in the catheter 10. Therefore, the axial rigidity of the catheter 10 can be improved, allowing the operator's pushing force to be efficiently transmitted to the distal end of the catheter 10. As a result, the catheter 10 can be easily delivered to a narrowed or obstructed segment of the lumen.

Further, as shown in FIG. 2C, the catheter 10 may include a portion in which a cross-sectional area of the second core wire is smaller than a cross-sectional area of the first core wire. In FIG. 2C, X1 represents the diameter of the first core wire 70, X2 represents the diameter of the second core wire 80, and X3 represents a distance between the outer tube 30 and the inner tube 50. There is thus a portion of the catheter 10 in which the diameter X1 of the first core wire 70 is equal to the distance X3 between the outer tube 30 and the first inner tube 50 (X1=X3), while the diameter X2 of the second core wire 80 is smaller than the distance X3 between the outer tube 30 and the first inner tube 50 (X2<X3). Therefore, both the frictional resistance between the second core wire 80 and the outer tube 30 and the frictional resistance between the second core wire 80 and the inner tube 50 can be reduced when the second core wire 80 moves depending on the external forces 1, 2, 3, and 4 exerted at a curved region of the lumen. Because the second core wire 80 can smoothly move to the optimal position, the risk is further reduced that the catheter 10 will get caught in a curved region of the lumen.

Figure 4:
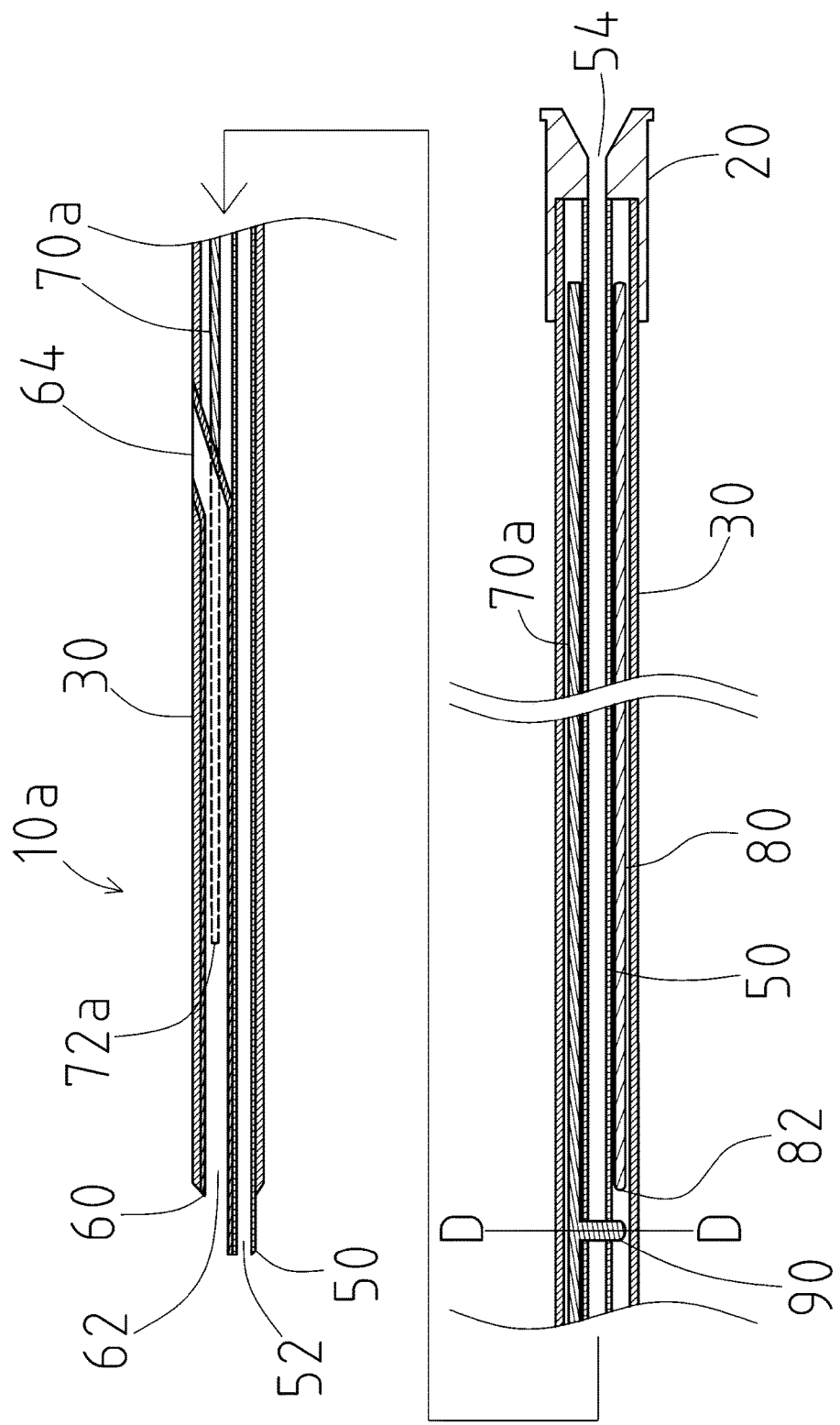
FIG. 4 shows an overall view of a catheter according to the disclosed embodiments.
Figure 5:
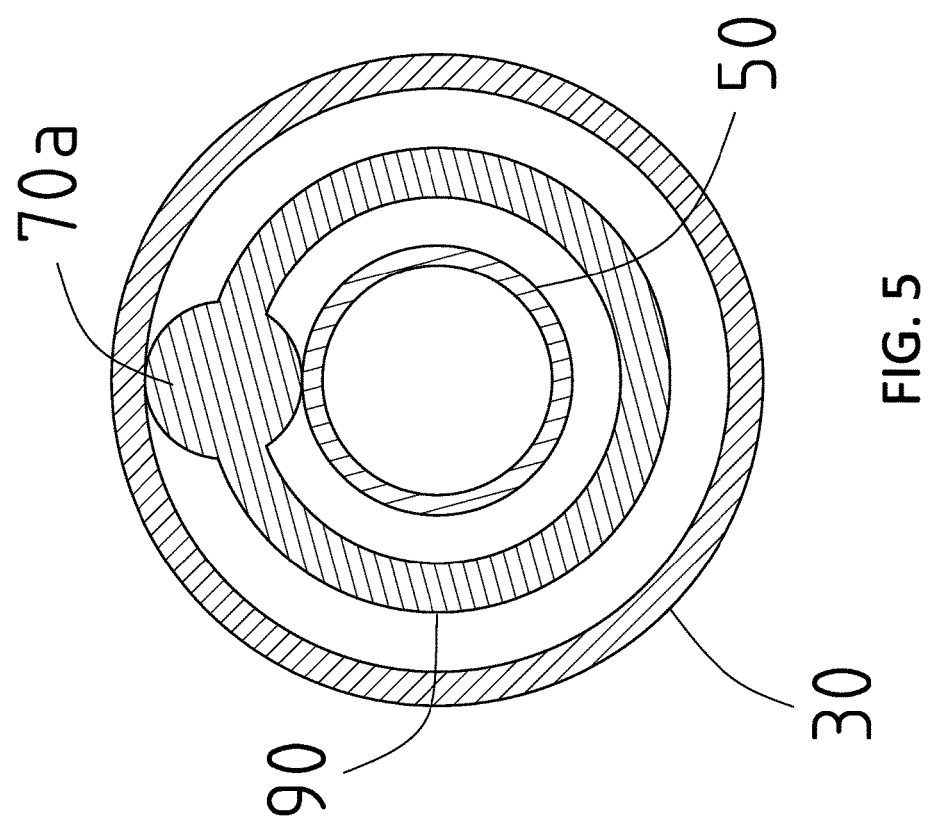
FIG. 5 is a cross-sectional view taken along line D-D of FIG. 4.

The catheter may include a restriction part located in a medial region of the first core wire, as described with reference to catheter 10a shown in FIGS. 4 and 5. Note that as in FIG. 1, the left side in FIG. 4 corresponds to the distal end (the front end), which is to be inserted into the body, and the right side corresponds to the proximal end (the base end), which is to be operated by an operator such as a physician. Note that FIG. 5 is a cross-sectional view taken along line D-D of FIG. 4.

Only differences from the catheter 10 shown in FIGS. 1 to 3 are described. As shown in FIGS. 4 and 5, the catheter 10a comprises an annular restriction part 90 in a medial region of a first core wire 70a. The restriction part 90 is located distally to the distal end 82 of the second core wire 80, and restricts the movement of the distal end of the second core wire 80 in the distal direction. Note that the distal end 72a of the first core wire 70a is located distally to the second insertion opening 64 of the second inner tube 60, as in the catheter 10.

There is no particular limitation for the material of the restriction part 90, but the restriction part 90 of the catheter 10a is formed with the same material as the first core wire 70a. Specifically, the restriction part 90 may be formed by welding an annular member comprising the same metal material as the first core wire 70a to the first core wire 70a. There is no particular limitation for the method of forming the restriction part 90, and the restriction part 90 may be formed, for example, by bonding an annular member comprising a resin material to the first core wire 70a using an adhesive agent.

Moreover, the restriction part 90 may be formed by melt-welding the outer tube 30 with the first inner tube 50 without using other members as long as the restriction part 90 can restrict the movement of the second core wire 80 in the distal direction by contacting the distal end 82 of the second core wire 80.

As described above, the movement of the second core wire 80 in the distal direction is restricted in the case of the catheter 10a because the restriction part 90 contacts the distal end 82 of the second core wire 80 when the operator pushes the catheter 10a in the distal direction. This reduces the risk that the distal end 82 of the second core wire 80 will project out of the outer tube 30 and/or break through the second inner tube 60. Moreover, a force that drives the second core wire 80 to move in the distal direction is transmitted to the first core wire 70a through the restriction part 90. Because the first core wire 70a in the catheter 10a is fixed to the outer tube 30 as in the catheter 10 (see FIG. 2B), the force can be transmitted through the restriction part 90 to the outer tube 30 via the first core wire 70a. This further improves the pushing force transmitted to the distal end of the catheter 10a.

The restriction part may be located at the proximal end of the second core wire, as described with reference to the catheter 10b shown in FIGS. 6 and 7. Note that as in FIG. 1, the left side in FIG. 6 corresponds to the distal end (the front end), which is to be inserted into the body, and the right side corresponds to the proximal end (the base end), which is to be operated by an operator such as a physician. Note that FIG. 7 is a cross-sectional view taken along line E-E of FIG. 6.

Only differences from the catheter 10 shown in FIGS. 1 to 3 are described. As shown in FIGS. 6 and 7, the catheter 10b comprises an annular restriction part 100 at a proximal end of a second core wire 80a. The restriction part 100 contacts a proximal end 74 of the first core wire 70, and restricts the movement of the second core wire 80a in the distal direction.

There is no particular limitation for the material of the restriction part 100, but the restriction part 100 of the catheter 10b is formed with the same material as the second core wire 80a. Specifically, the restriction part 100 may be formed by welding an annular member comprising the same metal material as the second core wire 80a to the proximal end of the second core wire 80a. There is no particular limitation for the method of forming the restriction part 100, and the restriction part 100 may be formed, for example, by bonding an annular member comprising a resin material to the second core wire 80a using an adhesive agent.

Moreover, the restriction part 100 may be formed by winding (proximal to the proximal end 74 of the first core wire 70) the proximal end of the second core wire 80a around the outer periphery of the first inner tube 50 without using other members. The restriction part 100 may be formed by other methods as long as the restriction part 100 can restrict the movement of the second core wire 80a in the distal direction by contacting the proximal end 74 of the first core wire 70.

As described above, in the case of the catheter 10b, the restriction part 100 provided at the second core wire 80a contacts the proximal end 74 of the first core wire 70 when the operator pushes the catheter 10b in the distal direction. This prevents the second core wire 80a from moving in the distal direction, which reduces the risk that the distal end 82a of the second core wire 80a will project out of the outer tube 30 and/or break through the second inner tube 60. Moreover, a force that drives the second core wire 80a to move in the distal direction is transmitted to the first core wire 70 through the restriction part 100. Because the first core wire 70 in the catheter 10b is fixed to the outer tube 30 as in the catheter 10 (see FIG. 2B), the force can be transmitted through the restriction part 100 to the outer tube 30 via the first core wire 70. This further improves the pushing force transmitted to the distal end of the catheter 10b. Furthermore, because the restriction part 100 of the catheter 10b is provided within the connector 20, the restriction part 100 does not project into the lumen. This further reduces the risk that the catheter 10b will get caught in a curved region of the lumen.

The restriction part may contact both the proximal end of the first core wire and the proximal end of the outer tube, as described with reference to catheter 10c shown in FIGS. 8 and 9. Note that as in FIG. 6, the left side in FIG. 8 corresponds to the distal end (the front end), which is to be inserted into the body, and the right side corresponds to the proximal end (the base end), which is to be operated by an operator such as a physician. Note that FIG. 9 is a cross-sectional view taken along line F-F of FIG. 8.

Figure 6:
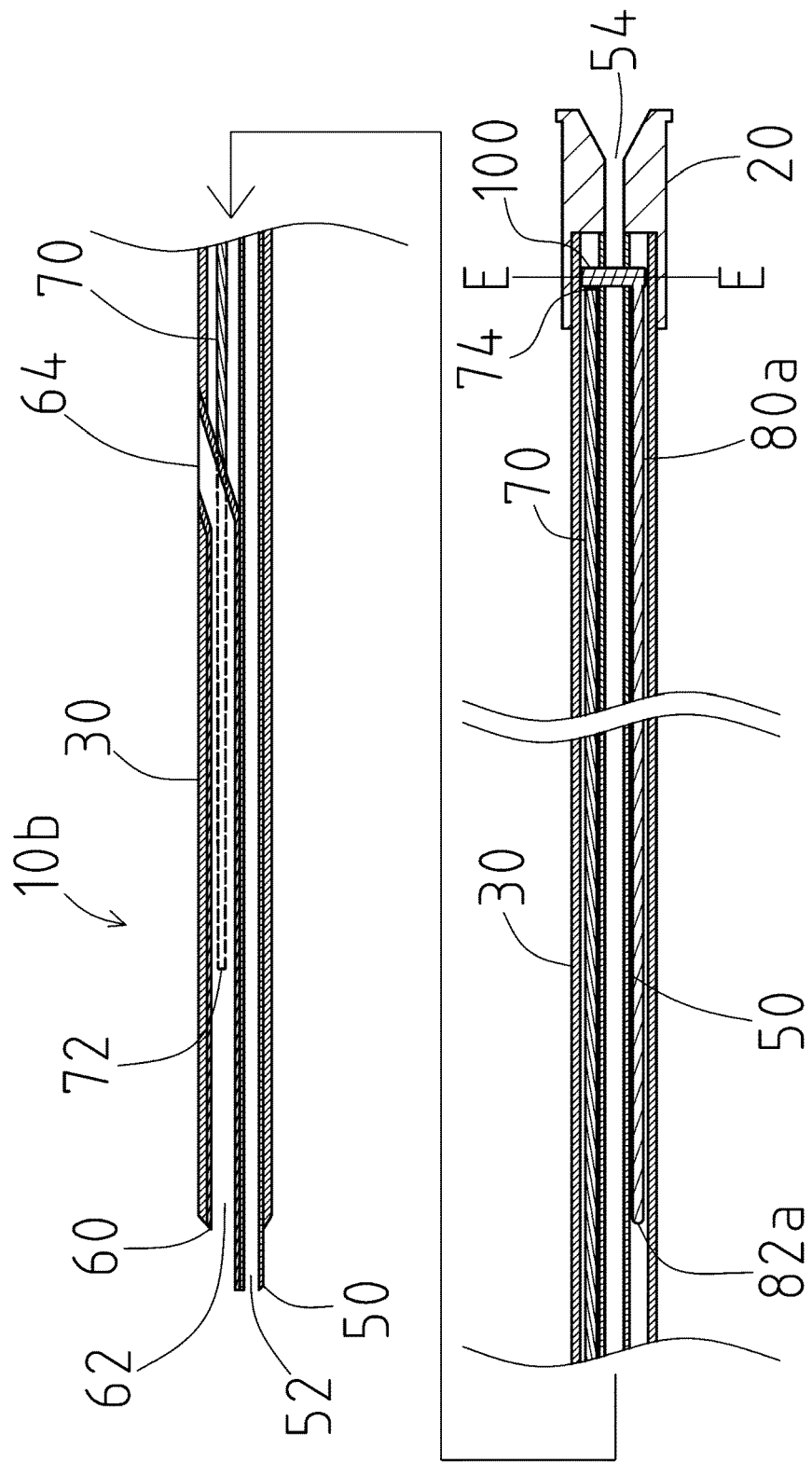
FIG. 6 shows an overall view of a catheter according to the disclosed embodiments.
Figure 7:
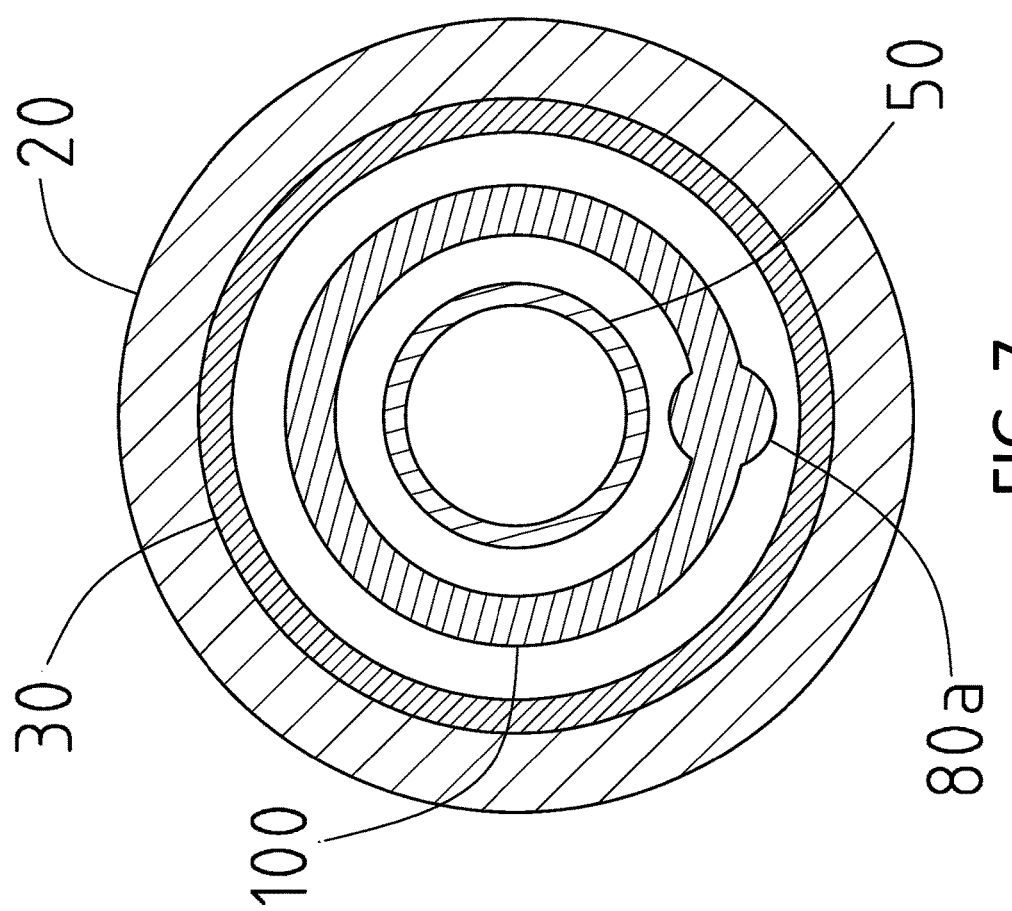
FIG. 7 is a cross-sectional view taken along line E-E of FIG. 6.

Only differences from the catheter 10b shown in FIGS. 6 and 7 are described. As shown in FIGS. 8 and 9, the catheter 10c comprises an annular restriction part 110 at a proximal end of a second core wire 80b. The restriction part 110 contacts the proximal end 74 of the first core wire 70 and a proximal end 34 of an outer tube 30a to restrict the movement of the second core wire 80b in the distal direction.

There is no particular limitation for the material of the restriction part 110. The restriction part 110 in the catheter 10c is formed with the same material as the second core wire 80b, as in the catheter 10b. Specifically, the restriction part 110 may be formed by welding an annular member comprising the same metal material as the second core wire 80b to the proximal end of the second core wire 80b. There is no particular limitation for the method of forming the restriction part 110, and the restriction part 110 may be formed, for example, by bonding an annular member comprising a resin material to the second core wire 80b using an adhesive agent.

Moreover, the restriction part 110 may be formed by winding (proximal to the proximal end 74 of the first core wire 70) the proximal end of the second core wire 80b around the outer periphery of the first inner tube 50 without using other members. The restriction part 110 may be formed by other methods as long as the restriction part 110 can restrict the movement of the second core wire 80b in the distal direction by contacting the proximal end 74 of the first core wire 70 and the proximal end 34 of the outer tube 30a.

As described above, in the case of the catheter 10c, the second core wire 80b is prevented from moving in the distal direction because the restriction part 110 provided at the second core wire 80b contacts the proximal end 74 of the first core wire 70 when the operator pushes the catheter 10c in the distal direction. This reduces the risk that the distal end 82b of the second core wire 80b will project out of the outer tube 30a and/or break through the second inner tube 60. Moreover, a force that drives the second core wire 80b to move in the distal direction can be transmitted to the first core wire 70 as well as the outer tube 30a through the restriction part 110. This further improves the pushing force transmitted to the distal end of the catheter 10c.

Figure 10:
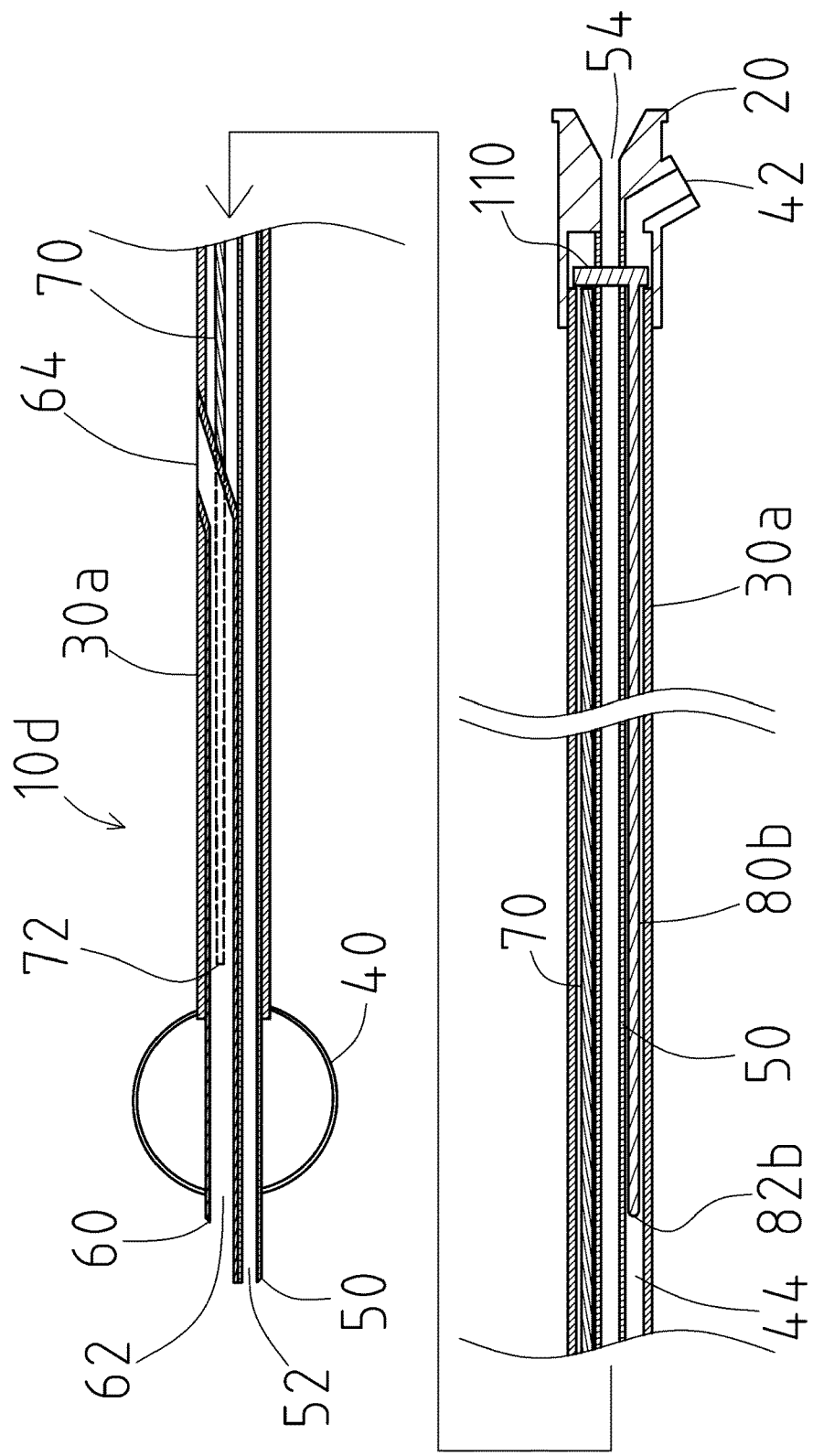
FIG. 10 shows an overall view of a balloon catheter according to the disclosed embodiments.

Next, a balloon catheter 10d of the disclosed embodiments is described with reference to FIG. 10. Note that as in FIG. 8, the left side in FIG. 10 corresponds to the distal end (the front end), which is to be inserted into the body, and the right side corresponds to the proximal end (the base end), which is to be operated by an operator such as a physician.

Figure 8:
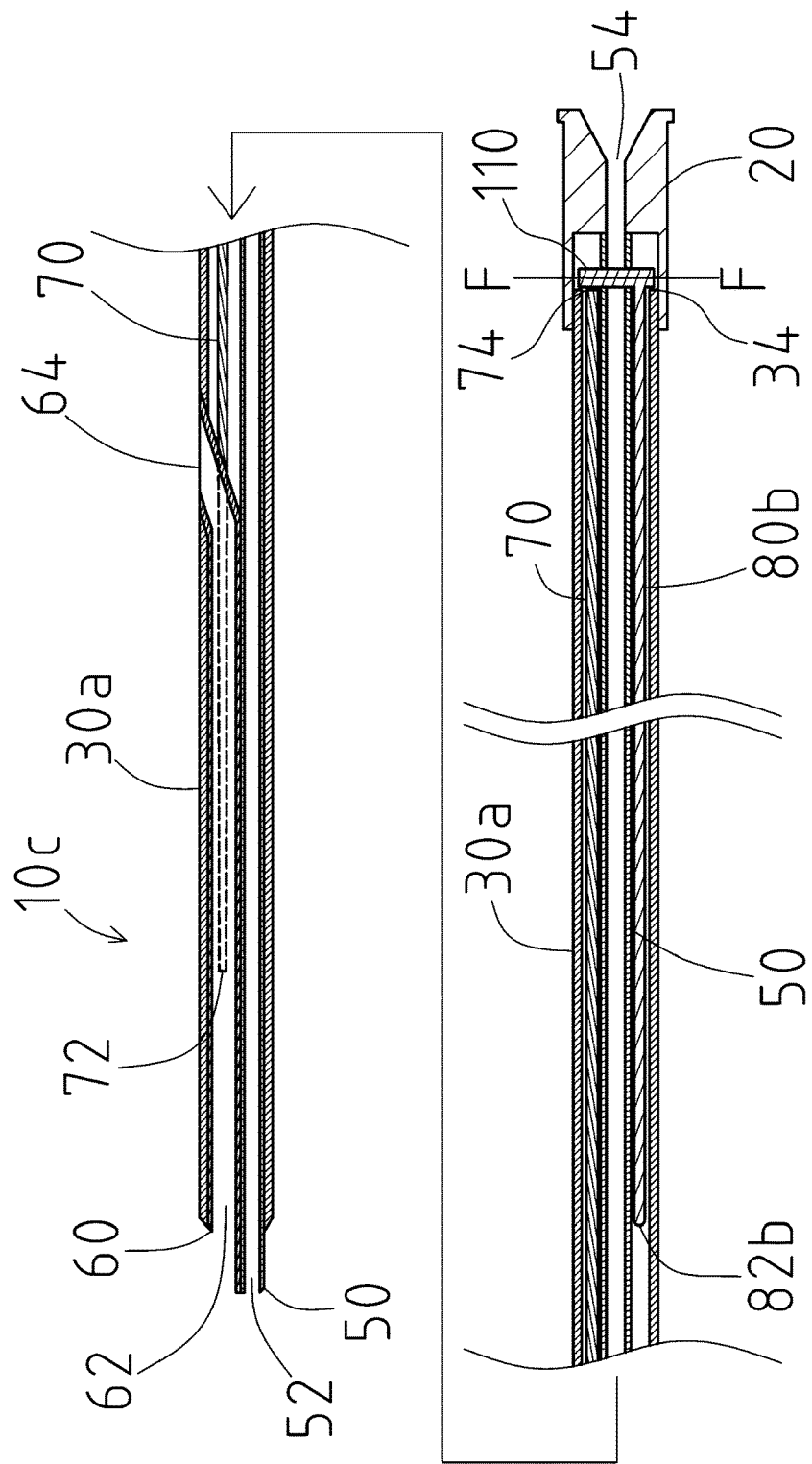
FIG. 8 shows an overall view of a catheter according to the disclosed embodiments.
Figure 9:
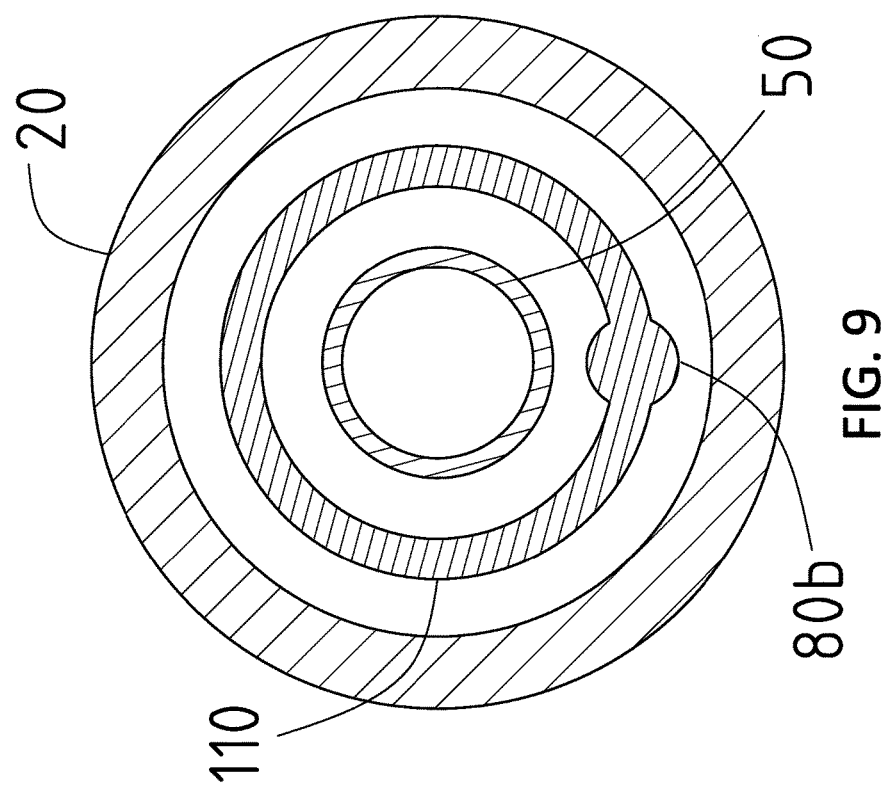
FIG. 9 is a cross-sectional view taken along line F-F of FIG. 8.

Only differences from the catheter 10c shown in FIGS. 8 and 9 are described. As shown in FIG. 10, the balloon catheter 10d comprises a balloon 40 fixed (e.g., by melt-welding) to a distal end of an outer tube 30a. A distal end of the balloon 40 is fixed (e.g., by melt-welding) to the first inner tube 50 and the second inner tube 60.

A supply opening 42 for supplying a liquid such as a contrast medium or physiological saline is provided at a connector 20, and an indeflator (not shown) may be attached to the supply opening 42. A liquid supplied from the indeflator is passed through an inflation lumen 44 formed with the outer tube 30 and the first inner tube 50 to inflate the balloon 40.

Unlike the catheters 10, 10a, 10b, and 10c, in the case of the balloon catheter 10d, the distal end of the balloon catheter 10d can be fixed by supplying a liquid from the supply opening 42 through the inflation lumen 44 to inflate the balloon 40 to the wall of a blood vessel, bile duct, pancreatic duct or the like. When a first guide wire inserted into the first inner tube 50 or a second guide wire inserted into the second inner tube 60 is operated while the balloon is inflated, the backup properties of the first guide wire or the second guide wire are improved because the distal end of the balloon catheter 10d does not move.

As described above, the catheters 10, 10a, 10b, 10c and the balloon catheter 10d have configurations where the second core wire 80, 80a, 80b can move to the optimal position depending on the external force 1, 2, 3, 4 exerted at a curved region of the lumen when the catheter 10, 10a, 10b, 10c or the balloon catheter 10d is inserted into the curved region of the lumen. This reduces the risk that the first core wire 70, 70a and the second core wire 80, 80a, 80b will interfere with each other, preventing the catheter 10, 10a, 10b, 10c or balloon catheter 10d from bending along the lumen and potentially breaking one or both of the first core wire 70, 70a and the second core wire 80, 80a, 80b.

Note that the first core wire 70, 70a may be fixed to the outer tube 30, 30a, as shown in FIG. 2B in the above description, but the configuration is not limited to this. The first core wire 70, 70a may be fixed to any one or both of the first inner tube 50 and the second inner tube 60 instead of the outer tube 30, 30a.

Moreover, the cross-sectional shapes of the first core wire 70, 70a and the second core wire 80, 80a, 80b shown in FIGS. 2A to 2C and FIG. 3 in the above description are both circular, but the shapes are not limited to this. For example, the cross-sectional shapes of the first core wire 70, 70a and the second core wire 80, 80a, 80b may be either elliptical or rectangular. However, in order to allow the second core wire 80, 80a, 80b to smoothly move to the optimal position depending on the external force 1, 2, 3, 4 exerted at a curved region of the lumen, the catheter 10, 10a, 10b, 10c or balloon catheter 10d includes a portion in which the cross-sectional area of the second core wire 80, 80a, 80b is smaller than a cross-sectional area of the first core wire 70, 70a.

What is claimed is:
1. A catheter comprising:
an outer tube;
a first inner tube disposed within the outer tube;
a second inner tube disposed within the outer tube and disposed parallel to the first inner tube, the second inner tube having an insertion opening provided at a proximal end of the second inner tube and a distal end opening provided at a distal end of the second inner tube;
a first core wire disposed between the outer tube and the first inner tube, the first core wire being fixed to the outer tube or the first inner tube; and
a second core wire disposed between the outer tube and the first inner tube, disposed parallel to the first core wire, and disposed outside the second inner tube, the second core wire being configured to move between the outer tube and the first inner tube, wherein:
the second inner tube extends from a medial region of the catheter to a distal end of the catheter, and
a distal end of the first core wire is located distal to the insertion opening of the second inner tube, and a distal end of the second core wire is located proximal to the insertion opening of the second inner tube.

2. The catheter according to claim 1, wherein the first core wire is longer than the second core wire.

3. The catheter according to claim 2, wherein a cross-sectional area of the second core wire is smaller than a cross-sectional area of the first core wire in at least a portion of the catheter when viewed in cross section.

4. The catheter according to claim 2, further comprising a restriction part provided at the first core wire or the second core wire, wherein the restriction part restricts distal movement of the second core wire.

5. The catheter according to claim 4, wherein the restriction part is provided at the second core wire, and is positioned proximal to a proximal end of the first core wire or a proximal end of the outer tube.

6. The catheter according to claim 1, wherein a cross-sectional area of the second core wire is smaller than a cross-sectional area of the first core wire in at least a portion of the catheter when viewed in cross section.

7. The catheter according to claim 6, further comprising a restriction part provided at the first core wire or the second core wire, wherein the restriction part restricts distal movement of the second core wire.

8. The catheter according to claim 7, wherein the restriction part is provided at the second core wire, and is positioned proximal to a proximal end of the first core wire or a proximal end of the outer tube.

9. The catheter according to claim 1, further comprising a restriction part provided at the first core wire or the second core wire, wherein the restriction part restricts distal movement of the second core wire.

10. The catheter according to claim 9, wherein the restriction part is provided at the second core wire, and is positioned proximal to a proximal end of the first core wire or a proximal end of the outer tube.

11. A balloon catheter comprising:
the catheter according to claim 1;
a balloon fixed to the outer tube and the first inner tube; and
a supply opening for supplying a liquid into the balloon.

12. A catheter comprising:
an outer tube;
a first inner tube disposed within the outer tube;
a second inner tube disposed within the outer tube and disposed parallel to the first inner tube, the second inner tube having an insertion opening provided at a proximal end of the second inner tube and a distal end opening provided at a distal end of the second inner tube;
a first core wire disposed between the outer tube and the first inner tube, the first core wire being fixed to the outer tube or the first inner tube;
a second core wire disposed between the outer tube and the first inner tube and disposed parallel to the first core wire, the second core wire being configured to move between the outer tube and the first inner tube; and
a restriction part provided at the first core wire or the second core wire,
wherein:
the second inner tube extends from a medial region of the catheter to a distal end of the catheter,
a distal end of the first core wire is located distal to the insertion opening of the second inner tube, and a distal end of the second core wire is located proximal to the insertion opening of the second inner tube, and
the restriction part restricts distal movement of the second core wire.

13. The catheter according to claim 12, wherein the restriction part is provided at the second core wire, and is positioned proximal to a proximal end of the first core wire or a proximal end of the outer tube.

14. The catheter according to claim 12, wherein the first core wire is longer than the second core wire.

15. The catheter according to claim 12, wherein a cross-sectional area of the second core wire is smaller than a cross-sectional area of the first core wire in at least a portion of the catheter when viewed in cross section.

16. A catheter comprising:
an outer tube;
a first inner tube disposed within the outer tube;
a second inner tube disposed within the outer tube and disposed parallel to the first inner tube, the second inner tube having an insertion opening provided at a proximal end of the second inner tube and a distal end opening provided at a distal end of the second inner tube;
a first core wire disposed between the outer tube and the first inner tube, the first core wire being fixed to the outer tube or the first inner tube; and
a second core wire disposed between the outer tube and the first inner tube and disposed parallel to the first core wire, the second core wire being configured to move between the outer tube and the first inner tube and to come in contact with the first core wire,
wherein:
the second inner tube extends from a medial region of the catheter to a distal end of the catheter, and
a distal end of the first core wire is located distal to the insertion opening of the second inner tube, and a distal end of the second core wire is located proximal to the insertion opening of the second inner tube.

* * * * *